(12) United States Patent
Kranovich

(10) Patent No.: US 7,026,018 B2
(45) Date of Patent: Apr. 11, 2006

(54) COATING WITH ANTI-MICROBIAL AGENT FOR REFRIGERATOR SHELVING

(75) Inventor: Richard L. Kranovich, Davenport, IA (US)

(73) Assignee: SSLO Holding Company, Inc., Fort Smith, AR (US)

( * ) Notice: Subject to any disclaimer, the term of this patent is extended or adjusted under 35 U.S.C. 154(b) by 0 days.

(21) Appl. No.: 10/416,943

(22) PCT Filed: Nov. 15, 2001

(86) PCT No.: PCT/US01/44795

§ 371 (c)(1),
(2), (4) Date: Oct. 8, 2003

(87) PCT Pub. No.: WO02/40180

PCT Pub. Date: May 23, 2002

(65) Prior Publication Data

US 2004/0052965 A1     Mar. 18, 2004

Related U.S. Application Data

(60) Provisional application No. 60/249,351, filed on Nov. 15, 2000.

(51) Int. Cl.
 *B05D 1/02*    (2006.01)
 *B05D 1/28*    (2006.01)
 *B05D 3/06*    (2006.01)

(52) U.S. Cl. ............... 427/521; 427/427.4; 427/427.7; 427/428.01

(58) Field of Classification Search ................ 427/508, 427/521, 428, 386, 389.9, 195, 202, 194, 427/428.01, 427.4, 427.7
See application file for complete search history.

(56) References Cited

U.S. PATENT DOCUMENTS

| 5,190,932 | A | * | 3/1993 | Dhein et al. |
| 5,670,261 | A | * | 9/1997 | Kameya et al. |
| 5,698,229 | A | * | 12/1997 | Ohsumi et al. |
| 5,980,620 | A | * | 11/1999 | Brodie et al. |
| 6,093,407 | A | * | 7/2000 | Cummings et al. |

FOREIGN PATENT DOCUMENTS

JP          09-189478      *  7/1997

* cited by examiner

*Primary Examiner*—Fred J. Parker
(74) *Attorney, Agent, or Firm*—Varnum, Riddering Schmidt & Howlett LLP

(57) ABSTRACT

The embodiments disclose means to inhibit the growth and migration of bacteria, mildew and fungus by applying various coatings which contain an inorganic anti-microbial agent onto metal, glass, and plastic substrates. The substrates are used in the manufacture of components for the interior of refrigerators and freezers, which include wire (100) and glass shelving (200, 300), plastic crisper baskets (500) and other articles within the food storage area. The coatings include the inorganic anti-microbial agent combinet with a matrix resin which are applied by electrostatic powder coating (916), roller coating (810), or robotic spraying (710), and then cured.

8 Claims, 9 Drawing Sheets

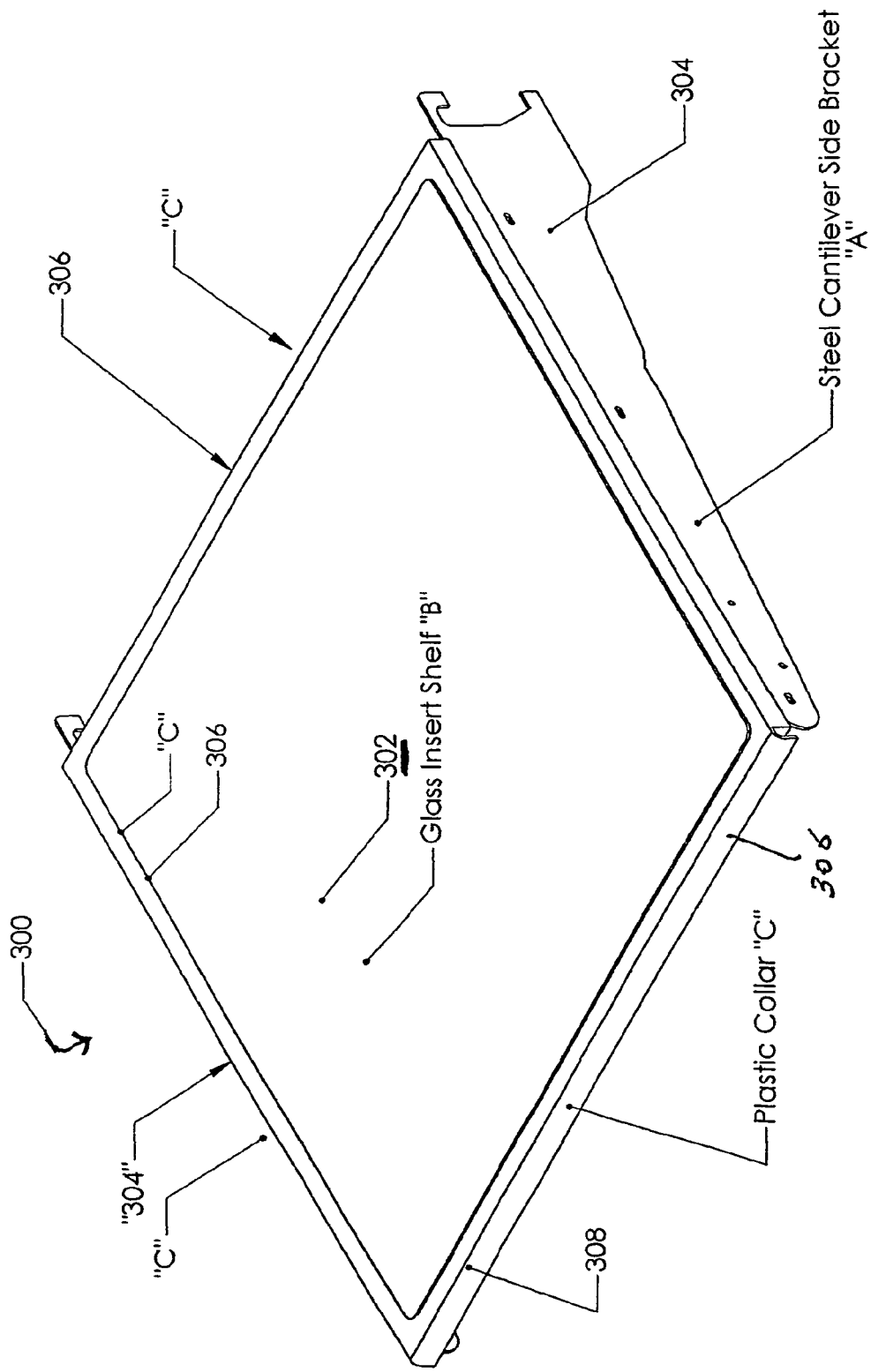
Fig. 2 : Cantilever Glass Shelf

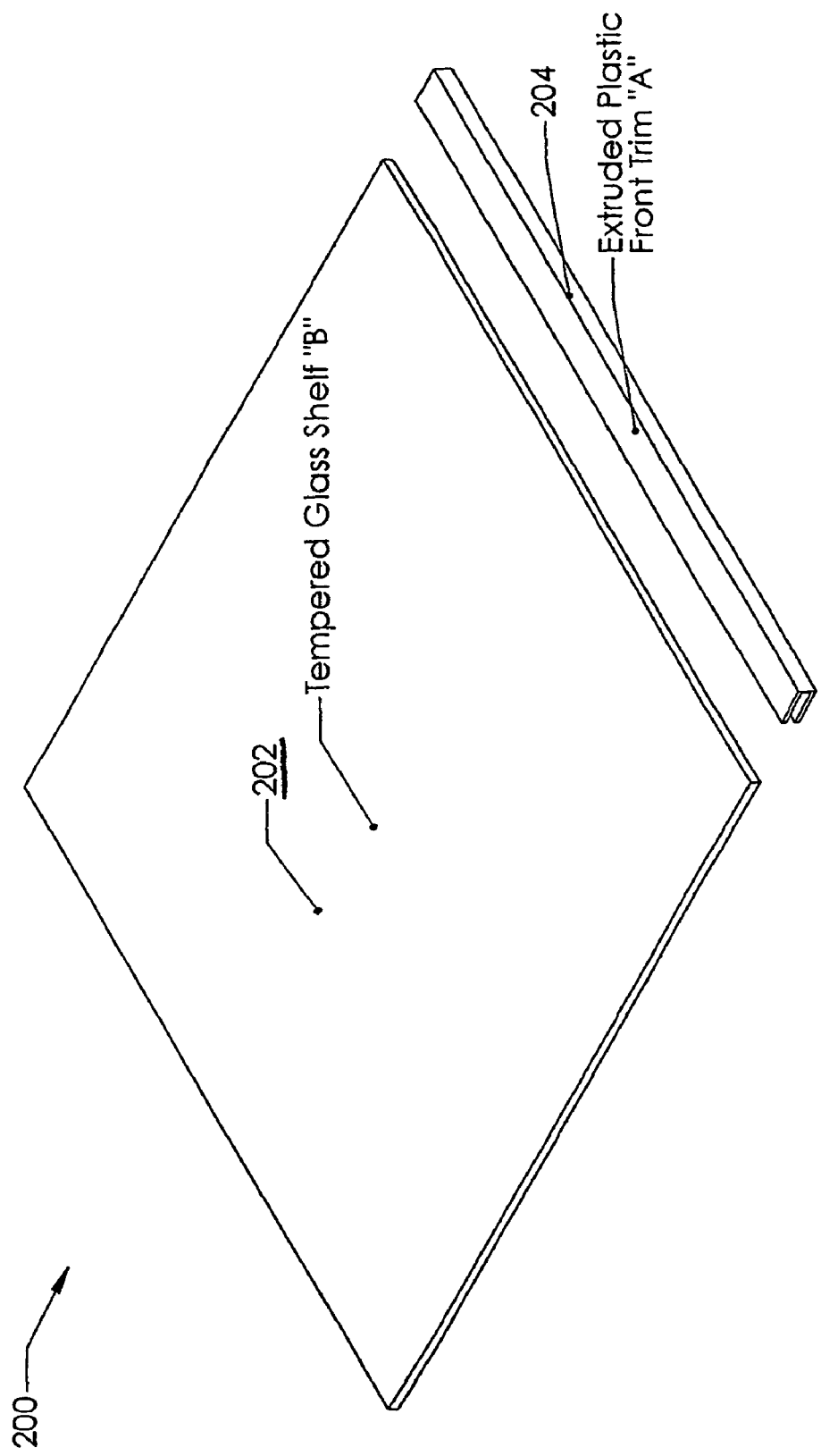
Fig 3.: Glass Shelf with Plastic Front Trim

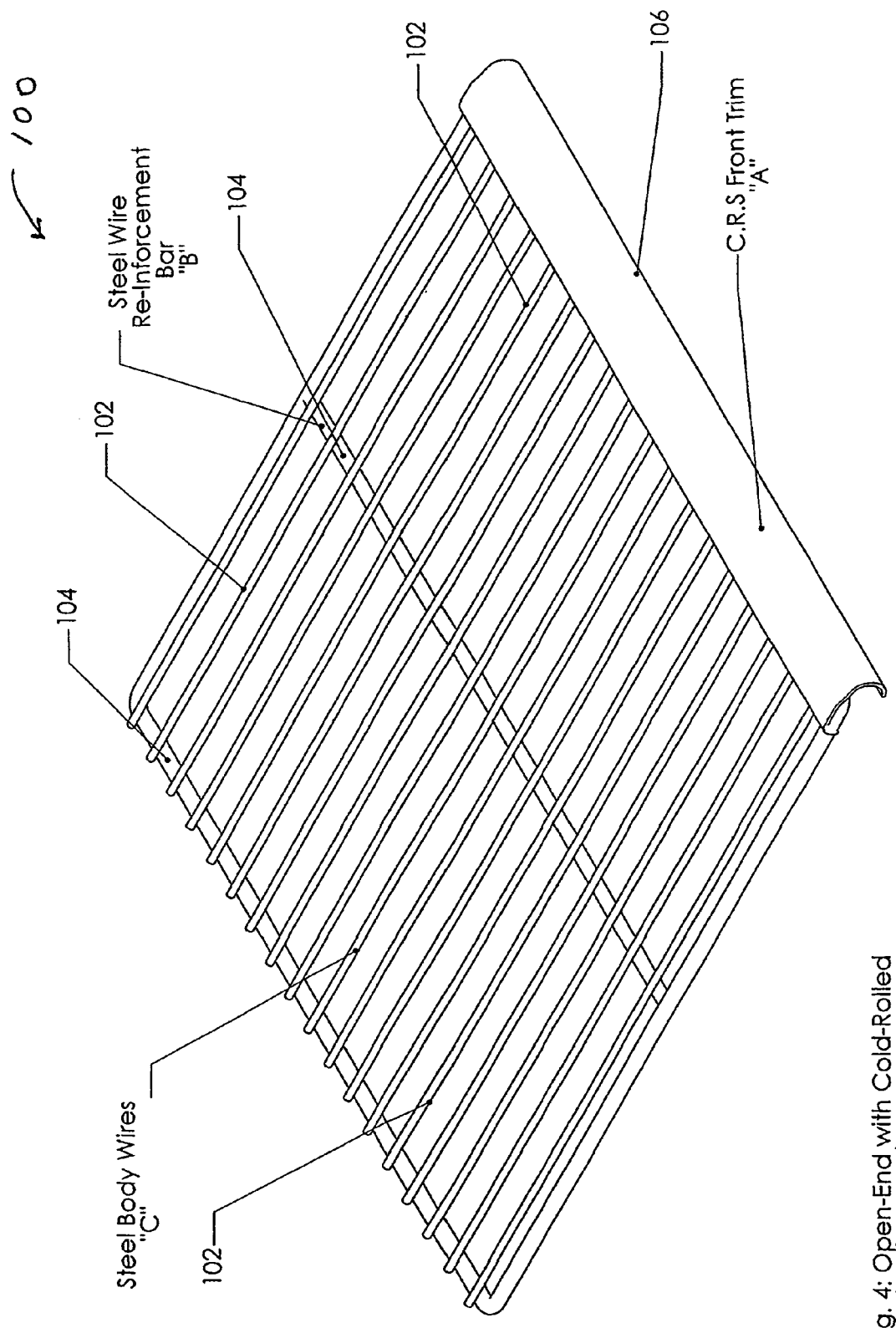
Fig. 4: Open-End with Cold-Rolled Steel Roll Formed Front Trim

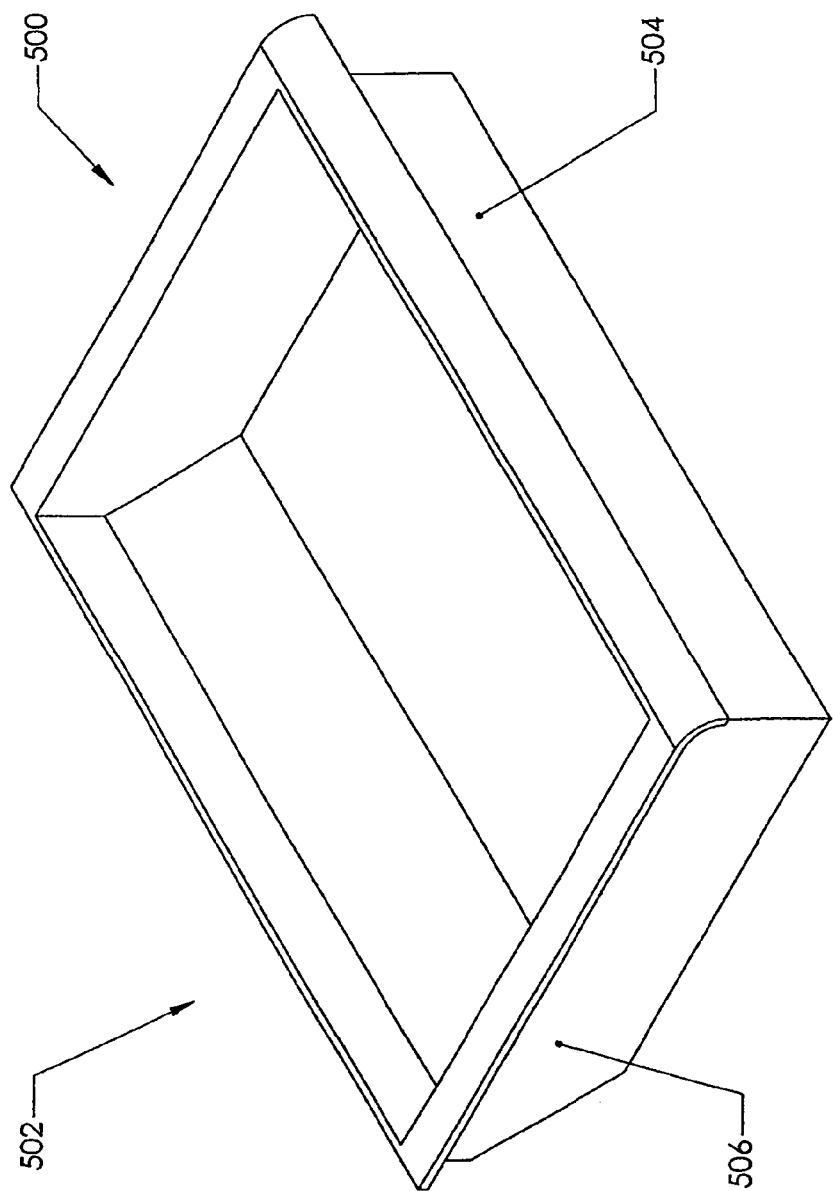
Fig. 5 : Plastic Crisper Basket (SAN) or (ABS)

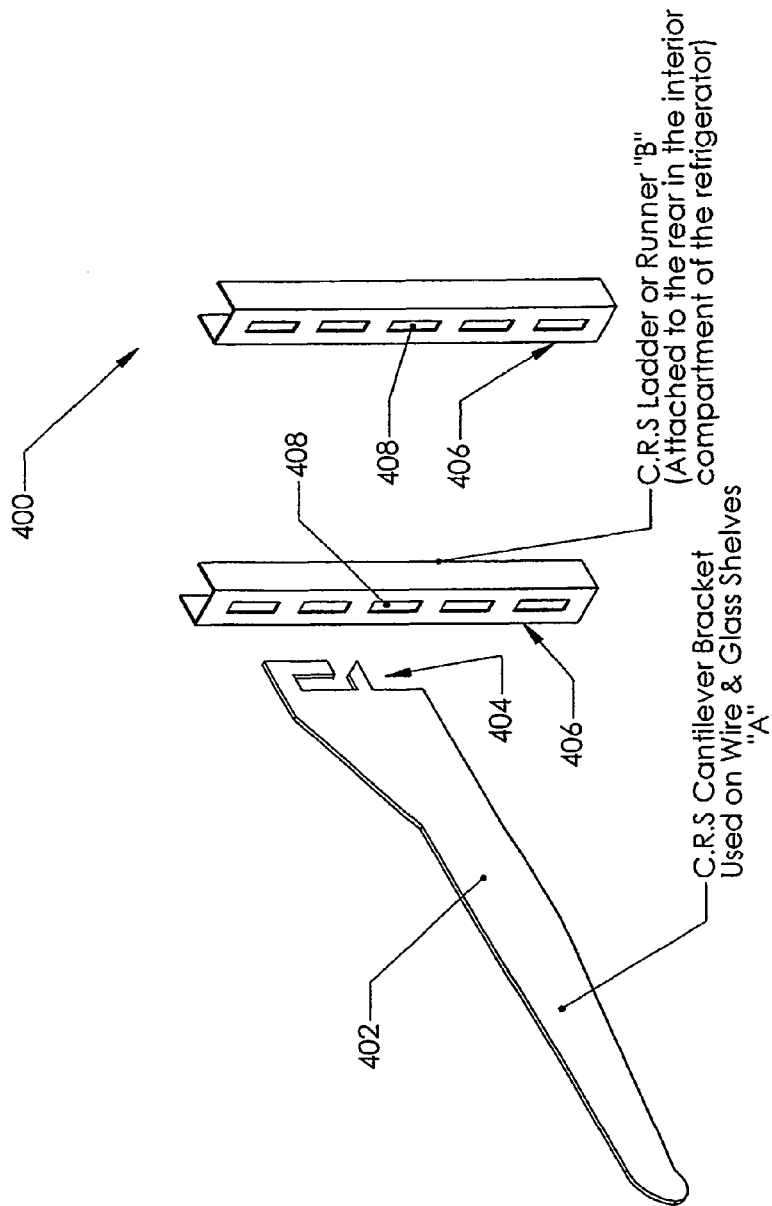
Fig 6.: Ladders or Runners for Cantilever Brackets - For Shelf Adjustability

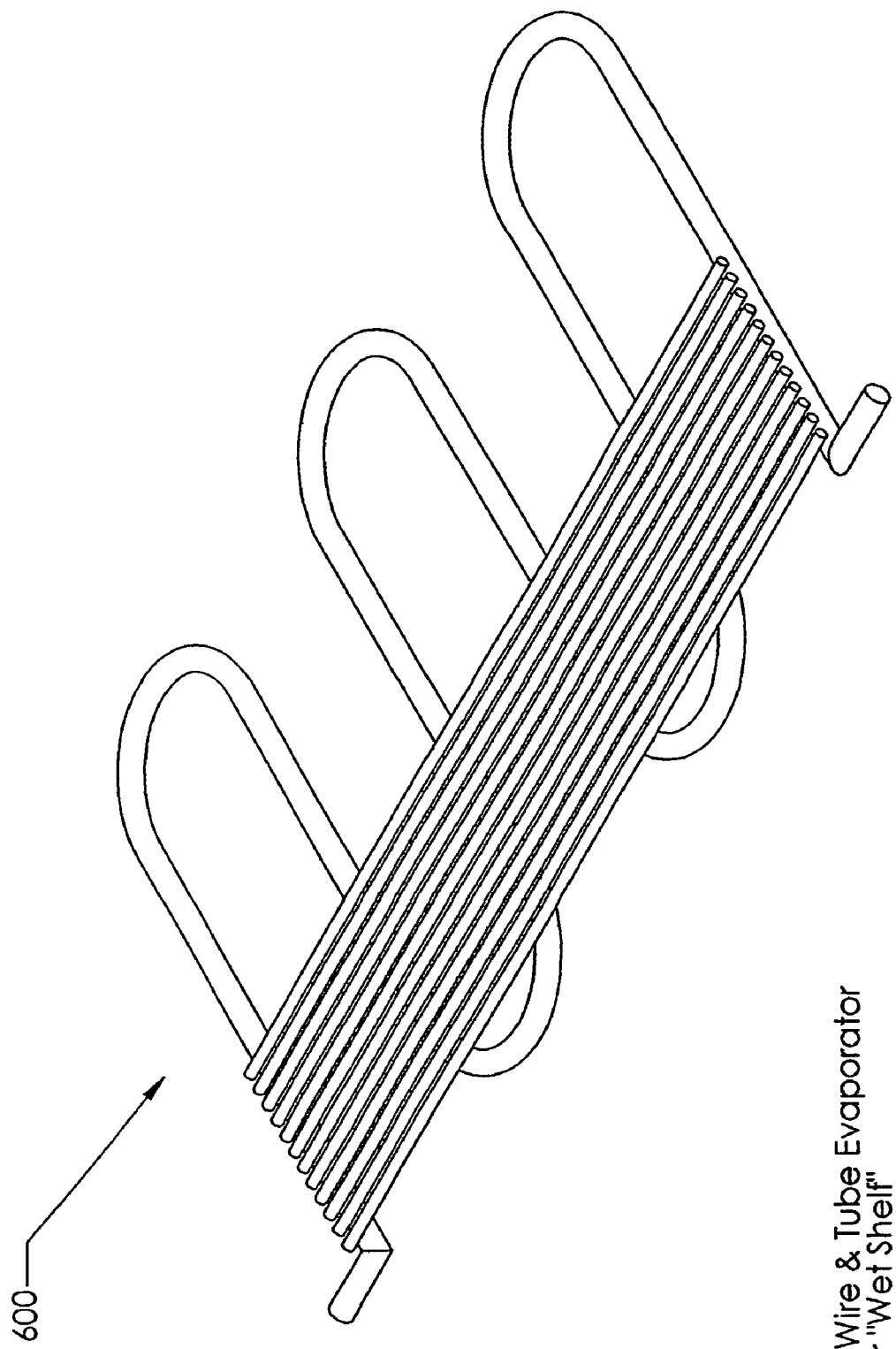
Fig. 7: Wire & Tube Evaporator Shelf or "Wet Shelf" For manuel defrost systems (Common in Europe)

COATING WITH ANTI-MICROBIAL AGENT FOR REFRIGERATOR SHELVING

CROSS-REFERENCE TO RELATED APPLICATIONS

This application claims priority of U.S. Provisional Patent Application Ser. No. 60/249,351, filed Nov. 15, 2000.

STATEMENT REGARDING FEDERALLY SPONSORED RESEARCH OR DEVELOPMENT

Not Applicable.

REFERENCE TO A MICROFISHE APPENDIX

Not Applicable.

BACKGROUND OF THE INVENTION

1. Field of the Invention

The invention relates to articles and processes involving various types of coatings comprising an anti-microbial agent and, more particularly, the use of coatings comprising an anti-microbial agent which may be applied to metal, glass and plastic substrates as found in refrigerator interiors.

2. Background Art

Refrigerator shelving, baskets, and other interior-related items are very susceptible to various types of bacteria, fungus and mildew. These refrigerator items are manufactured of materials such as metal, glass and plastic substrates. Spoiled foods can cause the surfaces of these substrates to be contaminated with various harmful bacteria, resulting in possible cross-contamination with other foods and migration of the harmful bacteria to adjacent areas of a shelf or onto other components attached to the shelf. In addition, when foods become spoiled, and in those instances when mildew and fungus may grow, offensive odors can occur. A refrigerator shut down over a period of time, and containing foods and liquids, becomes a perfect environment for the growth of mold and mildew; resulting not only in harmful bacteria but unpleasant odors as well. Thus, it would be advantageous to develop materials which could be applied to the aforedescribed refrigerator items, so as to eliminate or at least severely retard the breeding and migration of bacteria.

Currently, there are no known chemical compositions or procedures to readily prevent growth and migration of bacteria on refrigerator interior articles, where use of such compositions and procedures are also cost effective and comply with manufacturers' current shelf performance requirements. Systematic washing of refrigerator shelving and other interior components is one method of cleaning, which is often viewed by the consumer and user as time-consuming and bothersome. This is particularly true when trying to clean glass and plastic shelving where food particles may work their way into small corners or openings. Similarly, thorough cleaning of wire shelves is extremely difficult, since food particles may become lodged where the body wires are welded on top of center-support, reinforcement rods. Also, spraying of the above-mentioned articles by some liquid antiseptic or cleaners is considered to be a nuisance, since the shelving and other components need to be removed from the refrigerator so that proper spraying and cleaning can be achieved. Other more sophisticated cleaning methods may be employed that usually involve complex procedures not typically employed by a conventional user, such as high pressure steaming, antiseptic or solvent dipping and the like.

From a cost effectiveness position, it may not be economically feasible on some refrigerator parts such as plastic crispers to add the anti-microbial material to the plastic resin due to the size and the amount of the material required. Also, adding an anti-microbial agent to glass when it is in the molten state appears impractical, since it may be difficult to achieve a consistent, uniformed dispersion of the anti-microbial agent, particularly on the surface of the glass where it is needed to be effective. Thus, it would be advantageous to utilize a coating which would provide a practical, cost-effective method to integrate an anti-microbial agent with the surface of the article itself.

SUMMARY OF THE INVENTION

In accordance with the principles of the invention, a method is provided for imparting a coating, containing an anti-microbial agent onto low-carbon steel wire and other steel substrate interior refrigerator articles. The method includes blending the anti-microbial agent in a necessary proportion to an amount of thermosetting hybrid epoxy/polyester powder within a supply cartridge on an electrostatic powder coater. The steel substrate is then cleaned and followed by an iron or zinc phosphate or zinc plate process, and further followed with a chrome seal. The coating is then deposited with the anti-microbial agent at a thickness between 100 and 120 microns by electrostatic means using powder guns positioned within a booth. The coating is then cured in a direct, gas-fired convection oven to achieve proper crosslinking. Further in accordance with this aspect of the invention, the blending of the anti-microbial agent in a necessary proportion is in the amount of approximately 2.5%. The convection oven operates at a temperature of approximately 375° F. The time period for curing the coating in the convection oven is approximately 18 minutes. Still further, the anti-microbial agent may be one which is manufactured by AgIon Technologies.

A further method in accordance with the invention includes imparting the coating with the anti-microbial agent onto glass substrate interior refrigerator articles. The method includes adding the anti-microbial agent to a matrix containing an epoxy-acrylate resin, an adhesion promoter and a free-radical photo-initiator. The glass substrates are then cleaned and dried, and the coating is deposited to a thickness of approximately 20 microns by use of a roller-coater. The coating is then cured utilizing a UV processor.

In accordance with other aspects of this method, the step of adding the anti-microbial agent to the matrix utilizes a concentration of approximately 5%. The UV processor may have an output of approximately 400 watts per inch.

In accordance with another aspect of the invention, the coating may be imparted, with an anti-microbial agent, onto plastic substrates consisting of SAN, ABS, or PP for baskets, crisper drawers and other interior plastic articles as a part of refrigerator shelving or storage items. The method includes adding the anti-microbial agent to a matrix, containing a resin, adhesion promoter and free-radical photo-initiator. The plastic substrates are then cleaned and dried, and the coating is deposited to a thickness of approximately 20 microns though the use of a programmable robotic spray. The coating is then cured utilizing a UV processor containing Honley UV lamps. The step of adding the agent to the matrix may utilize a concentration of approximately 5%. The step of curing the coating using a UV processor may utilize a UV processor with a dual zone containing six Honley UV lamps.

The invention may also include the method of facilitating a safer biological environment for interior refrigerator articles. The method includes the steps of combining different coatings with a silver-based anti-microbial agent. Differing application processes are then utilized for applying the coatings combined with the agent to the interior refrigerator articles, with the interior refrigerator articles composed of various material substrates. The substrates can include wire and steel, glass and plastic.

Also in accordance with this method, color dyes may be added to the coatings for the glass substrates in order to enhance appearance. Patterns may be added to the glass coatings, such as straight or wavy lines, circles and similar patterns by designing patterns on a coating roller in order to enhance appearance.

The method in accordance with the invention may also include blending the agent with a thermosetting powder paint and applying the coating in a manner so as to withstand the harsh rigors of refrigeration components, and to maintain efficacy of the agent upon the surfaces of the wire and steel articles. In addition, the method can include the step of adding the agent to a resin and applying the coating to certain glass and plastic substrates, in a manner so as to withstand the harsh rigors of refrigerator requirements, and to maintain efficacy of the agent upon the surfaces of the glass and certain plastic substrates used on the articles.

The method can also include the step of adding the agent to a resin and applying the coating to certain glass and plastic substrates in a manner so as to provide clarity and a relatively high level of transparency in accordance with refrigerator manufacturers' requirements. The agent can also be added to a powder and a resin, with the coatings applied to the substrates in a manner so as to resist certain stains in accordance with refrigerator manufacturer' components.

BRIEF DESCRIPTION OF THE SEVERAL
VIEWS OF THE DRAWINGS

The invention will now described with reference to the drawings in which:

FIG. 1(D) illustrates an end view of the roller coater of FIG. 1(B);

FIG. 2 is a perspective view of a cantilever glass shelf which may be employed as a refrigerator article for which a method of integrating an anti-microbial agent with the surface of the article may be employed, in accordance with the invention;

FIG. 3 is a perspective view of a glass shelf with plastic front trim, which also may be employed in accordance with the invention in a manner similar to that of the refrigerator shelving illustrated in FIG. 2;

FIG. 4 is a perspective view of a wire shelf characterized as an open-end shelf with cold-rolled steel roll formed front trim;

FIG. 5 is a perspective view of a plastic crisper basket which may be employed in a refrigerator and which may be coated using procedures in accordance with the invention;

Figure 1A:
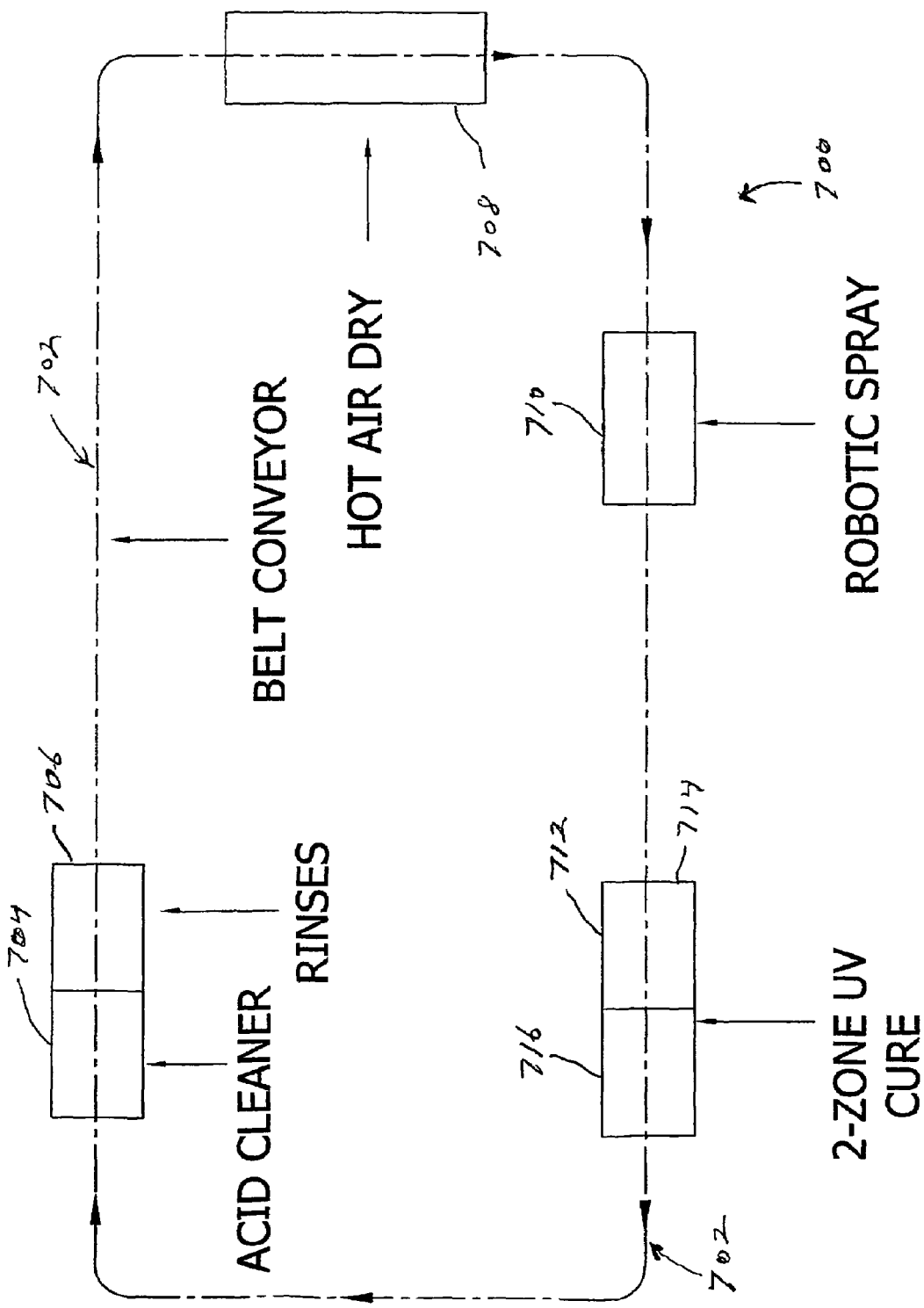
FIG. 1(A) illustrates a functional and structural block diagram of a system for applying a liquid coating to plastic substrates (including ABS, SAN and PP), such as the crisper drawers shown in FIG. 5 and baskets by a robotic spray method.

FIG. 6 illustrates several views of ladders or runners which may be utilized for cantilever brackets, so as to provide shelf adjustability, with the articles in FIG. 6 being adapted to be employed with refrigerator articles illustrated in certain of the prior views; and FIG. 7 is a perspective view of a wire and tube evaporator shelf, which is often characterized as a "wet shelf," and may be adapted for use in manual defrost systems of refrigerators.

DETAILED DESCRIPTION OF THE INVENTION

The principles of the invention are disclosed, by way of example, in embodiments as described in subsequent paragraphs herein and as illustrated in the drawings. The principles of the invention involve the use of an inorganic anti-bacterial material. As of this time, the inventor is unaware of any particularly good organic agent which may be used in accordance with the invention. However, the inventor also believes that such organic agents may exist or otherwise be subsequently developed, and may be utilized in the future in accordance with certain principles of the current invention.

Further, the principles of the invention involve various methods of imparting an anti-microbial agent to a wide variety of interior refrigerator articles, such as wire shelves, wire baskets, glass shelves, plastic crisper drawers, cantilevers shelf supports, wire wine racks, trivets, dividers and many other similar items. Key objectives, which comprise the spirit of the invention, involve achieving a practical and cost-effective solution in providing a safer refrigerator interior environment to the consuming public.

An anti-microbial agent which may be utilized with coatings in accordance with the invention is silver based and commercially available from AgIon Technologies. The selected anti-microbial agent, in accordance with the invention, is added to various coating materials and then applied to various substrates, such as steel wire, glass and plastic. With the addition of the anti-microbial agent to various coating materials, an anti-microbial property is imparted to various articles associated with refrigerator and freezer compartments.

A first embodiment of the present invention includes the addition of the anti-microbial material to epoxy/polyester hybrid powders which are electrostatically applied to low-carbon steel wire that has been resistance welded and assembled into numerous models and shapes. These models and shapes serve as refrigerator shelving and/or forms, trivets, baskets, dividers or racks. They may be stamped, cold-rolled steel cantilever brackets and roll-formed steel sections, also resistance welded to a wire assembly. As an example, FIG. 4 illustrates a wire shelf 100 which may be manufactured in accordance with the foregoing. The wire shelf 100 may consist of steel body wires 102 which are arranged in a parallel configuration and interconnected through the use of steel wire reinforcement bars 104. In addition, as further illustrated in FIG. 4, the wire shelving 100 may include a cold-rolled steel front trim 106. After coating, the parts are cured in a bake oven. In this embodiment, the wire refrigeration shelf 100 is coated with an epoxy-polyester powder paint. The anti-bacterial agent can be integrated with the resin or in this application is blended or flocked as an additive in proper proportions to the resin.

This anti-microbial agent can also be applied to other thermal setting polymer powder paints, which include: polyesters, epoxy, epoxy-polyesters, polyurethanes, and acrylics. Also, this anti-microbial agent can be added within the family of thermoplastic powder paint materials, such as polyethylene, nylon, polypropylene, ethylvinyl acetate, polyvinyl acetate, and polyvinyl chloride.

The second embodiment of the invention includes the addition of the anti-microbial agent to a coating composition that is applied to the surface of refrigerator glass shelving. This coating composition can consist of a matrix made of epoxy-acrylate, an adhesion promoter which is a functional silane, a free-radical photo-initiator and the silver based anti-microbial agent. The liquid coating may be applied by roller, curtain, or spray to the glass shelving and cured by UV light. However, in this application, roller coating is the preferred method of coating a flat glass article. An example of glass shelving which may be utilized with this type of coating is illustrated in FIG. 3 as glass shelf 200. The shelf 200 may consist of a tempered glass portion 202, with an extruded plastic front trim 204 releasably connected thereto. Another type of glass shelf which may be utilized in accordance with the invention is illustrated in FIG. 2 as cantilever glass shelf 300. As shown specifically in FIG. 2, the cantilever glass shelf 300 can include a rectangular glass insert 302. The glass insert 302 is encompassed with a plastic collar 306. For purposes of releasably interconnecting the cantilever glass shelf 300 to frame parts of the refrigerator, a system shown as cantilever system 400 in FIG. 6 may be utilized. The cantilever system 400 includes cantilever side brackets 402 which would correspond to the side brackets 304 illustrated in FIG. 2. The side brackets 402 include interconnecting elements 404 which can be manually and releasably interconnected with ladders or runners 406 also shown in FIG. 6. The ladders or runners 406 may be attached to the rear or other frame portions in the interior compartment of a refrigerator. The ladders or runners 406 include a series of spaced apart slots 408 located at various vertical positions. The height of shelves interconnected to the cantilever brackets 402 may be adjusted by selectively positioning the interconnection elements 404 into the slots 408.

A third embodiment in accordance with the invention can include the same coating chemistry as described above for the second embodiment. This coating is applied to substrates of styrene acrylonitrile copolymer (SAN) which is the base material for plastic crisper baskets or drawers in many refrigerator interiors, sometimes referred to as vegetable, fruit, meat, or deli drawers or crispers. The application method may comprise spraying the interior of the crisper drawers or baskets and curing by UV light. Spraying is generally the most prevalent method of application due to the numerous sizes and shapes of various interior refrigerator articles. Refrigerator articles which are employed in accordance with this third embodiment includes articles such as the plastic crisper basket 500 illustrated in FIG. 5. The crisper basket 500 may be formed of clear plastic having a partially angled rear portion 502, front portion 504 and interconnecting side portions 506.

A fourth embodiment in accordance with the invention can include the same coating chemistry as described for the second and third embodiments. This coating is applied to interior refrigeration articles made from acrylonitrile butadiene styrene polymer (ABS) and polypropylene (PP) articles such as refrigerator door trays or vents, egg and butter trays, slides or tracks, attachments to shelves, and in some European models, defrost trays. Spraying is often the most efficient method of applying the coating, followed by UV curing. A refrigerator article in accordance with the fourth embodiment can include the crisper basket 500 illustrated in FIG. 5, with the crisper basket made from ABS.

As an example of a further refrigerator article with which coating procedures in accordance with the invention may be utilized is the wire and tube evaporator shelf 600, illustrated in FIG. 7. The evaporator shelf 600 is often referred to as a "wet shelf" and is utilized with manual defrost systems. In particular, such shelving is relatively common in European refrigeration equipment and some U.S. upright freezers.

The introduction of an inorganic anti-microbial agent to various coatings which are applied to different material substrates should preferably meet a number of requirements. These requirements are described in accordance with the following examples. More specifically, coatings utilized with the introduction of inorganic anti-microbial agents should be chosen based on at least the following reasons:

1. Costs should be considered when coatings are selected as a means of imparting an anti-microbial agent to an article. This is particularly the case when dealing with interior refrigeration articles constructed of (SAN), (PP) or (ABS) materials. To injection mold these articles with the anti-microbial agent added would add costs that likely could not be recovered in the market place.

2. The introduction of an anti-microbial agent compounded into a plastic resin could affect the color requirements (white) on some parts and the clarity or transparency of other parts. Thus, coatings become a more practical solution to impart an anti-microbial property to articles previously defined.

3. As to steel and glass substrates, high processing temperatures prevent adding the anti-microbial agent to the composition.

As earlier described, an anti-microbial agent which may be utilized in accordance with the invention and which is commercially available may be acquired through AgIon Technologies. One type of anti-microbial agent which may be utilized and acquired through AgIon Technologies is classified as type AJ10D Silver Zeolite A. It is specifically designed to be incorporated into the materials previously listed. This type, zeomic AJ10D, is an odorless fine white powder insoluble in water. The composition includes sodium aluminosilicate (zeolite), silver, zinc and ammonium. This material (compound) possesses a true specific gravity of 2.1 and a pH in the range of 7–9 (1 g zeomic/100 ml water). Measured by atomic absorption spectrophotometry, the silver weight by percentage is $2.5\pm0.1$ and the zinc weight is $14.4\pm0.7$. Particle size is less than 5.0 microns (mean). The material is stable up to 850° C. The silver is released through ion exchange and lasts for the product life, being a very long-lived material. This material, when mixed with the epoxy-polyester resin, imparts an anti-microbial activity to the coating. The coating may then be applied by a conventional electrostatically sprayed powder system paint onto the metal (steel) substrates comprising the articles previously listed, such as wire shelves, forms, cantilever brackets, baskets, tracks, etc. The coating can then be cured at approximately 375° F. for 17 minutes in a gas oven.

The coating should preferably withstand rigorous testing to insure that product specifications and performance requirements are met. Various types of exemplary tests may be utilized to insure compliance with requirements.

For example, coated articles may be submitted to a certified laboratory so that the efficacy of the anti-microbial agent may be evaluated. Preferably, a "kill rate" of over 99% should be achieved. Upon achievement of this requirement, proper integration of the anti-microbial agent with the resin has occurred based on a 13–15 year life. The surface of a wire shelf is subject to considerable use. Thus, the coating must demonstrate strong abrasion resistant characteristics. Consequently, the part may then be subjected to a falling sand test (ASTM D968). Since this part (steel wire shelf) does not possess sufficient surface area to conduct appropriate testing, a flat steel section may be used instead. A steel specimen with the coating was exposed to 40 liters of falling sand. After abrading the part the amount of coating removed amounted to approximately 35 microns. The part was then re-submitted for efficacy testing. *Escherichia coli* was the test organism utilized. The incubation period was 24 hours. Results revealed that the coating continued to be effective with a kill rate of over 99%.

The following additional tests were performed:

| Test | Test Method | Result |
|---|---|---|
| Hardness of Coating | ASTM D363 | HB Scratch (passed) H Gouge (passed) |
| Cross hatch Adhesion | ASTM D3359 | 1/16" & 1/32" (passed) |
| Grease | 1/2 internal oleic acid & 1/2 cottonseed oil immersion at 75° F. wash off - no change in gloss, hardness, or appearance | (passed) |
| Salt Spray | ASTM B117 | 1/16" max creepage (passed) |
| Humidity | ASTM D2247 | 1/31" max. creepage (passed) |
| Coating Thickness | ASTM E376 ASTM 1186 | 4–5 mils (passed) |
| Stain | Internal (9 different stains) | (passed) |
| Taste & Odor | Internal | (passed) |

Furthermore, appearance characteristics such as gloss and color were not adversely affected by the integration of the anti-microbial agent with the coating.

The foregoing test results indicate the successful application of a thermosetting or thermoplastic resin with an anti-microbial agent to wire and steel shelving and other internal metal components as may be found in residential and commercial refrigerators.

On glass refrigerator shelving and on (SAN), (ABS) and (PP) plastic crisper baskets/drawers, tracks and slide assemblies, front trims and similar articles, the anti-microbial agent may be mixed with a composition of epoxy-acrylate, a silane to promote adhesion to the glass and a photo-initiator as referred to in the second, third, and fourth embodiments previously described. The anti-microbial agent, supplied by AgIon Technologies, may be a type zeomic AJ10K. The material is the same as AJ10D used in the epoxy-polyester formulation, with the exception that the silane content weight by percent is 5.0±0.1. This anti-microbial agent is then mixed with an epoxy-acrylate composition containing a functional silane and photo-initiators. This composition is sprayed on top of the glass, on the surfaces of ABS plastic articles and on the inside of crisper drawers made from SAN material. The coating, after curing, will have a thickness of approximately 20 microns.

The application processes for the plastic, glass and wire/steel articles may be functionally described with reference to the systems 700, 800 and 900, respectively, as illustrated in a block diagram format in FIGS. 1(A), 1(B) and 1(C), respectively.

More specifically, FIG. 1(A) represents a method which may be utilized for applying the coating to plastic substrates (SAN, ABS and PP) that have been previously identified as plastic crisper baskets, plastic shelving or other interior plastic components. The system 700 as functionally illustrated in FIG. 1(A) may utilize a palletized conveyor 702. The conveyor 702 may be a conventional belt conveyor onto which is loaded one or more pallets (not shown) which rest on the conveyor 702. The plastic parts to be coated are then loaded onto the pallets. The conveyor 702 will transport the pallets and conveyed parts through various "machine zones." With further reference to FIG. 1(A), the plastic part enters a first stage or first machine zone where an acid cleaner 704 is utilized to clean each plastic part. Preferably, the cleaner has a pH between 5.0–5.5. The cleaned plastic parts are then carried into a rinse area 706 which preferably includes an ambient rinse with pre-circulated DI water, followed by two virgin DI rinses. Thus, system component 706 comprises multiple rinses.

After rinsing, the belt conveyor 702 conveys the rinsed plastic parts through a dry-off oven (commonly known as a "hot air dry" oven) 708. The oven 708 preferably operates at a temperature of approximately 130° F. Following the drying of the plastic parts, the plastic parts continue on the conveyor 702 to a spray booth which comprises a robotic spray system 710. In the spray booth 710, the liquid coating is sprayed upon the plastic parts. The liquid coating is preferably applied by spraying through the use of a six-axis robot, having a programmable controller. Following the coating process, the plastic parts continue on the conveyor 702 and enter a curing chamber which is referred to as a two-zone UV cure apparatus 712. As an example of a curing apparatus which may be used as apparatus 712, the curing apparatus or chamber may house four Honley UV lamps in a first cure zone 714, and two Honley UV lamp in a second cure zone 716. Upon completion of the curing, the plastic parts continue on the conveyor 702 until removed from the conveyor 702 for purposes of packing.

Figure 1B:
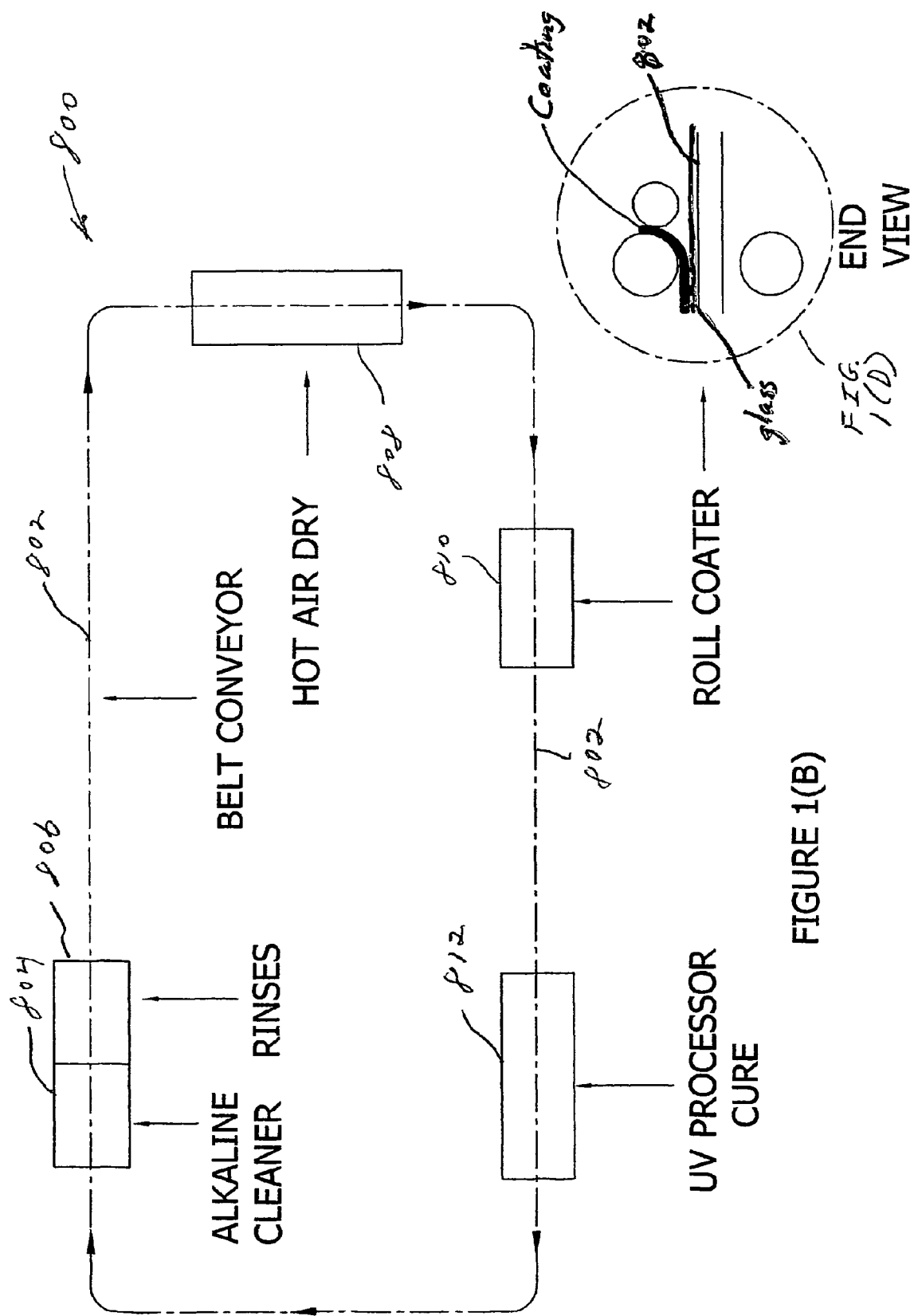
FIG. 1(B) illustrates a functional and structural block diagram of a system for applying a liquid coating to flat glass items (such as shown in FIG. 2 and FIG. 3) by a roller-coating method.

As earlier stated, the functionally and structurally illustrated system 800 in FIG. 1(B) comprises a system for applying a liquid coating to flat glass items, such as those illustrated in FIGS. 2 and 3. The process for this application of liquid coating is referred to as a roller-coating method. More specifically, FIG. 1(B) represents a method for applying the coating to glass substrates that have been previously identified as glass refrigerator shelves. In a manner similar to that shown in FIG. 1(A), the system 800 includes a belt conveyor 802 on which pallets (not shown) and glass substrates to be coated are loaded. The glass to be coated then passes through an alkaline cleaner 804. Preferably, the alkaline cleaner 804 possesses a pH in the range of 8.0–9.0. The glass part to be coated then moves from the alkaline cleaner 804 to rinses 806 similar to the rinses 706 described with respect to FIG. 1(A). That is, the rinses 806 include an ambient rinse with re-circulated DI water, followed by two virgin DI rinses. The glass part to be coated then moves on the conveyor 802 from the rinses 806 to a hot air dry oven 808. The hot air dry oven 808 operates in a manner similar to the hot air dry oven 708 also described with respect to FIG. 1(A).

Following the drying cycle, the glass part to be coated proceeds on the conveyor 802 to a roller coater stage 810. At the roller coater stage 810, the liquid coating is applied to the top-side of the glass article to be coated. As somewhat functionally and structurally illustrated in FIG. 1(D), the roller coater stage 810 includes a conventional coating roll, "doctor" roll and "idler/conveyor" roll.

After application of the liquid coating to the top-side of the glass by the roller coater stage 810, the glass shelf moves further on the conveyor 802 to a UV processor curing stage 812. For curing of the liquid coating applied to the glass shelf, the UV processor curing stage 812 preferably includes a UV processor having a 50 inch lamp housing, for purposes of providing approximately 400 watts per inch output. Following the curing stage 812, the glass shelf parts are removed from the conveyor 802. After the coating process for the glass shelf, plastic components can then be assembled onto the glass. In any event, the glass shelving, after removal from the conveyor 802, can be assembled and/or packed for shipping.

Figure 1C:
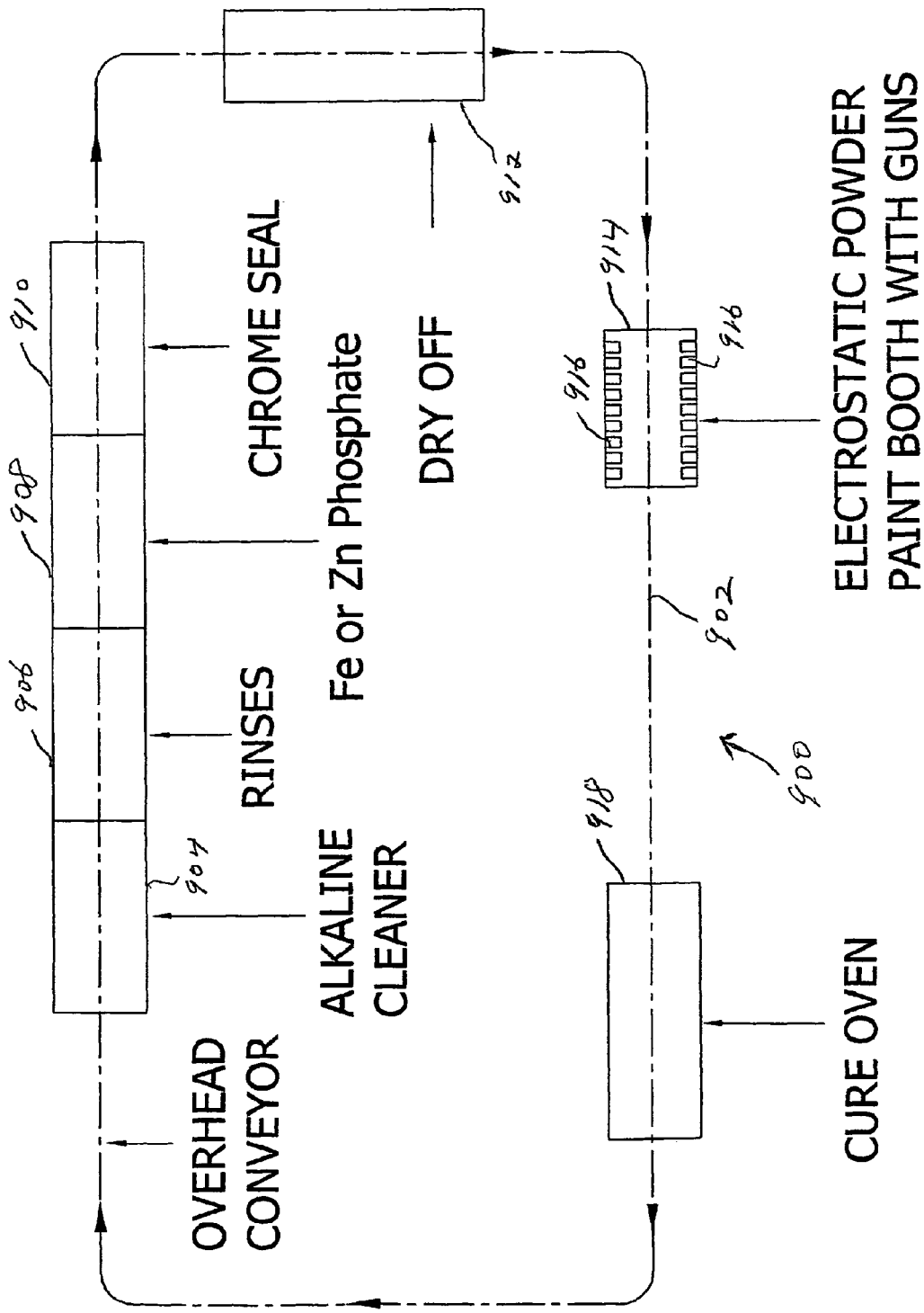
FIG. 1(C) illustrates a functional and structural block diagram of a system for applying powder coatings to wire and steel shelves, and other steel components by the electrostatic spray method.

As previously stated, FIG. 1(C) illustrates a system for applying powder coatings to wire and steel shelves, and other steel components. As with systems 700 and 800 illustrated in FIGS. 1(A) and 1(B), respectively, system 900 includes a conveyor 902, such as a conventional overhead conveyor. More specifically, the system 100 illustrates a method for applying a thermosetting, hybrid epoxy/polyester powder paint, with anti-microbial agents, to steel wire and steel component substrates previously identified as wire shelving, wire baskets, trivets, and similar refrigerator interior parts. Somewhat unlike systems 700 and 800 previously described, the refrigerator shelving and similar articles are hung onto racks (not shown) which, in turn, are hung to the overhead conveyor 902.

The parts to which the powder paint is to be applied are then moved through use of the conveyor 902 to an alkaline cleaner 904, similar to the alkaline cleaner 804 previously described with respect to FIG. 1(B). That is, the alkaline cleaner preferably possesses a pH in the range of 8.0–9.0. Also, the cleaner preferably is at a temperature of approximately 140° F.

Following cleaning through the alkaline cleaner 904, the parts are rinsed through the use of rinses 906. The rinses 906 can include an ambient rinse with re-circulated DI water followed by two virgin DI rinses. After proceeding through the rinses 906, the parts continue on the conveyor 902 where they are applied to a pre-treating apparatus 908. In the pre-treating apparatus 908, the parts are pre-treated with an iron or zinc phosphate or alkaline zinc plate. After application through the pre-treater 908, the conveyor 902 moves the parts into a sealer apparatus 910. In the apparatus 910, the parts are preferably sealed with a chrome-type sealer. Following the sealing process, the parts move on the conveyor 902 to a dry-off oven 912. The dry-off oven 912 operates in a manner similar to the oven 708 previously described with respect to FIG. 1(A). Following the dry-off process, the conveyor 902 moves the parts to an electrostatic powder paint booth 914. The paint booth 914 is conventional in function and structure, and applies the coating through the use of a series of automated spray guns 916. Following this application process, the conveyor 902 moves the painted parts to a cure oven 918. The cure oven 918 may comprise a direct, gas-fired convection oven. In this type of an oven, the parts are preferably cured at 375° F., for approximately 17 minutes. Following the curing process through the use of the cure oven 918, the parts can then be moved on the overhead conveyor 902 to a removal area, and packed for shipping.

The foregoing describes several exemplary systems for applying coatings through processes in accordance with the invention. As earlier stated, one important aspect of the coatings having the anti-microbial agents is the successful passing of a variety of tests. The following paragraphs briefly describe some of the aspects associated with these tests.

The coatings, with the anti-microbial agent, will preferably meet a specification requirement for abrasion. For glass and plastic parts, the test specimens must pass a 2 liter falling sand test with no breakdown to substrate per ASTM D968. Efficacy testing is conducted after the coating has been abraded. Certified lab results indicate that when exposed to *Escherichia coli* with an incubation period of 24 hours, the coating and the agent continue to be effective with a kill rate of over 99%.

The coatings on glass and plastic are subjected to the same tests as for metal listed earlier with the exception that for clarity, the tests are visual according to developed standards.

For further clarification, the stain tests applied to both the coating for metal substrates and the coating for glass and plastic substrates (ABS and SAN) may include the following:

Parts are stained with the following substances and kept under a watch glass at a temperature between 70 and 80° F.
  (a) unsalted butter,
  (b) 1% citric acid solution;
  (c) coffee;
  (d) anthraquinone violet R dye;
  (e) ethyl alcohol;
  (f) red lipstick;
  (g) yellow mustard;
  (h) tea;
  (i) 0.5% sodium hydroxide solution; and
  (j) grape juice.

Parts are then cleaned (washed with mild soap solution) Parts are then checked for staining.

In accordance with the foregoing, the invention is directed to the application of an epoxy-acrylate coating with an anti-microbial agent to glass and plastic parts within residential and commercial refrigerators. The invention is also directed to applying an epoxy-acrylate with an anti-microbial agent to both glass and plastic components as they relate to components within refrigeration compartments.

It will be apparent to those skilled in the pertinent art that other embodiments of the process described herein in accordance with the invention may be utilized. That is, the principles of imparting an anti-microbial agent to a wide variety of interior refrigerator articles are not limited to the specific embodiments described herein. Accordingly, it will be apparent to those skilled in the art that modifications and other variations of the above-described illustrative embodiments of the invention may be effected without departing from the spirit and scope of the novel concepts of the invention.

What is claimed is:

1. A method of imparting a coating, containing an anti-microbial agent onto glass substrate interior refrigerator articles, the method comprising the steps of:
  a. adding the anti-microbial agent to a coating formulation containing an epoxy-acrylate resin, an adhesion promoter, and a free-radical photo-initiator;
  b. cleaning and drying the glass substrates;
  c. depositing the coating formulation to a thickness of approximately 20 microns by the use of a roller-coater; and
  d. curing the deposited coating utilizing a UV processor.

2. The method in accordance with claim 1, in which the step of adding the anti-microbial agent to the coating formulation utilizes a concentration of approximately 5% by weight.

3. The method in accordance with claim 1, in which the anti-microbial agent is a sodium aluminosilicate.

4. The method in accordance with claim 1, in which the UV processor is of an output of approximately 400 watts per inch.

5. A method of imparting a coating, containing an anti-microbial agent onto plastic substrates consisting of styrene acrylonitrile copolymer (SAN), acrylonitrile butadiene styrene (ABS) or polypropylene (PP) for baskets, crisper drawers, and other interior plastic articles as a part of refrigerator shelving or storage items, the method comprising the steps of:

a. adding the anti-microbial agent to a coating formulation containing an epoxy-acrylate resin, an adhesion promoter, and a free-radical photo-initiator;

b. cleaning and drying the plastic substrates;

c. depositing the coating formulation to a thickness of approximately 20 microns by the use of a programmable robotic spray; and d. curing the deposited coating using a UV processor.

6. The method in accordance with claim 5, in which the step of adding the anti-microbial agent to the coating formulation utilizes a concentration of approximately 5% by weight.

7. The method in accordance with claim 5, in which the anti-microbial agent is a sodium aluminosilicate.

8. The method in accordance with claim 5, in which the step of curing the coating using a UV processor utilizes a UV processor with an output of approximately 400 watts per inch.

* * * * *